United States Patent
Yagi

(10) Patent No.: US 9,829,447 B2
(45) Date of Patent: Nov. 28, 2017

(54) X-RAY FLUORESCENCE ANALYZER AND METHOD OF DISPLAYING SAMPLE THEREOF

(71) Applicant: HITACHI HIGH-TECH SCIENCE CORPORATION, Minato-ku, Tokyo (JP)

(72) Inventor: Isao Yagi, Tokyo (JP)

(73) Assignee: Hitachi High-Tech Science Corporation (JP)

( * ) Notice: Subject to any disclaimer, the term of this patent is extended or adjusted under 35 U.S.C. 154(b) by 204 days.

(21) Appl. No.: 14/833,665

(22) Filed: Aug. 24, 2015

(65) Prior Publication Data
US 2016/0061753 A1 Mar. 3, 2016

(30) Foreign Application Priority Data
Aug. 28, 2014 (JP) ................. 2014-173681

(51) Int. Cl.
| | |
|---|---|
| G01N 23/04 | (2006.01) |
| G01N 23/22 | (2006.01) |
| G01N 23/223 | (2006.01) |
| G06T 11/00 | (2006.01) |
| G06T 7/00 | (2017.01) |
| H04N 5/321 | (2006.01) |

(52) U.S. Cl.
CPC ....... *G01N 23/223* (2013.01); *G01N 2223/61* (2013.01); *G01N 2223/633* (2013.01)

(58) Field of Classification Search
CPC ................. G01N 223/61; G01N 2223/633
See application file for complete search history.

(56) References Cited

U.S. PATENT DOCUMENTS

| | | | | |
|---|---|---|---|---|
| 5,105,452 A | * | 4/1992 | McInerney | A61B 6/032 378/19 |
| 5,181,513 A | * | 1/1993 | Touboul | A61B 5/02007 600/443 |
| 5,933,211 A | * | 8/1999 | Nakasugi | B82Y 10/00 355/18 |
| 6,295,333 B1 | * | 9/2001 | Tamura | G01N 23/223 378/44 |

(Continued)

FOREIGN PATENT DOCUMENTS

JP 2009-25241 A 2/2009

*Primary Examiner* — David J Makiya
*Assistant Examiner* — Soorena Kefayati
(74) *Attorney, Agent, or Firm* — Brinks Gilson & Lione

(57) ABSTRACT

An X-ray fluorescence analyzer includes a sample stage, a sample moving mechanism, an X-ray source, a detector detecting a fluorescent X-ray generated from the sample irradiated with a primary X-ray, an imaging device imaging the sample, a display device displaying the image on a screen, a pointing device designating a specific position on the screen for allowing an input at the specific position, an image processing device displaying a mark at the input position on the screen by the pointing device and a control device controlling the sample moving mechanism and the image processing device and, when the sample stage is moved, controlling the image processing device to display the mark on the screen with moving the mark in the same moving direction as that of the sample stage by the same moving distance.

8 Claims, 2 Drawing Sheets

(56) References Cited

U.S. PATENT DOCUMENTS

| | | | | |
|---|---|---|---|---|
| 6,614,533 | B1* | 9/2003 | Hata | G01J 3/2823 |
| | | | | 250/559.07 |
| 6,992,780 | B2* | 1/2006 | Sentoku | G03F 7/70233 |
| | | | | 250/548 |
| 7,177,391 | B2* | 2/2007 | Chapin | B65G 21/14 |
| | | | | 250/360.1 |
| 7,366,282 | B2* | 4/2008 | Peschmann | G01N 23/04 |
| | | | | 378/46 |
| 7,732,791 | B2* | 6/2010 | Ando | G01N 23/225 |
| | | | | 250/492.1 |
| 7,841,772 | B2* | 11/2010 | Nishii | A61B 6/08 |
| | | | | 378/206 |
| 7,856,081 | B2* | 12/2010 | Peschmann | G01N 23/223 |
| | | | | 378/46 |
| 9,207,156 | B2* | 12/2015 | Ariga | G01N 3/42 |
| 9,435,076 | B2* | 9/2016 | Medoff | C10L 5/442 |
| 2015/0170109 | A1* | 6/2015 | Sakuragi | B65G 43/02 |
| | | | | 705/7.25 |
| 2015/0208039 | A1* | 7/2015 | Kuga | G06T 15/20 |
| | | | | 348/46 |

* cited by examiner

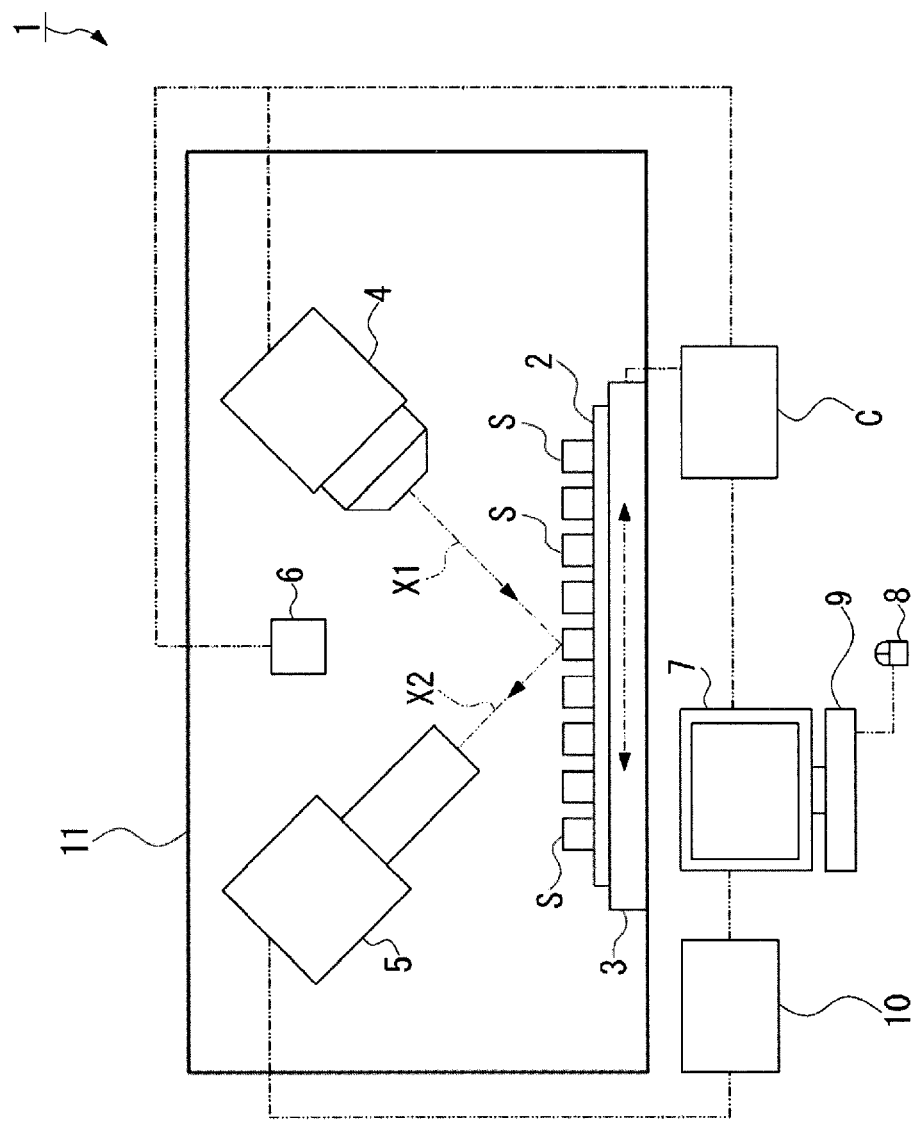

X-RAY FLUORESCENCE ANALYZER AND METHOD OF DISPLAYING SAMPLE THEREOF

RELATED APPLICATIONS

This application claims priority from Japanese Patent Application No. 2014-173681 filed on Aug. 28, 2014, the entire subject-matter of which is incorporated herein by reference.

TECHNICAL FIELD

The present disclosure relates to an X-ray fluorescence analyzer which is capable of, for example, detecting harmful substances and thus is used to screen a product or is used to measure a film thickness such as plating, and a method of displaying a sample of the X-ray fluorescence analyzer.

BACKGROUND

Fluorescent X-ray analysis is performed by irradiating a sample with an X-ray which is emitted from an X-ray source, detecting a fluorescent X-ray which is a characteristic X-ray discharged from the sample by an X-ray detector, and acquiring spectra from the energy of X-ray fluorescence so as to perform qualitative or quantitative analysis of the sample, or to measure the film thickness. The fluorescent X-ray analysis is capable of being rapidly carry out without destroying the sample, and thus is widely used in processing and quality control or the like. In recent years, it has been possible to realize microdetermination with high-sensitivity and high-precision, and thus particularly, the fluorescent X-ray analysis has been expected to be widely used as an analyzing method of detecting harmful substances which are included in a material, a composite electronic component, or the like.

In the related art, in such a fluorescent X-ray analyzer, a sample which is placed on a sample stage is checked through an image obtained by an imaging device such as an observation camera, the positioning of the sample is performed by moving the sample stage by a moving mechanism such as an XY stage, and then measurement or analysis is performed (for example, JP-A-2009-25241). Particularly, in a case where each of a plurality of samples which have the same shape as each other are placed on the sample stage so as to be measured, an operator counts the number of samples on a screen while moving the XY stage in such a manner that a predetermined sample is positioned by the movement of the XY stage to come to a measurement position.

In the related art described above, the following problems still remain.

In the X-ray fluorescence analyzer of the related art, the operator is required to match the position of the sample with a predetermined position of the sample stage, and the specific positioning of the sample is performed through an image obtained by a sample-observation camera; however, as illustrated in FIG. 3B, when the sample stage is moved, for example, in a case where each of a plurality of samples S which have the same shape as each other in a line are measured in certain intervals as illustrated in FIG. 3A, it is difficult to recognize which of the samples S is being checked though a camera image. That is, the operator visually counts the number of samples S in the camera image, and chooses the samples S to be measured so as to perform the positioning. For this reason, the operation becomes complicated and it is less likely that confirmation of whether or not the measuring point is correct can be achieved.

SUMMARY

Illustrative aspects of the present disclosure provide an X-ray fluorescence analyzer and a method of displaying a sample thereof, which are capable of improving the workability when each of a plurality of samples has the same shape as each other or when line patterns are measured at a certain interval and easily confirming whether or not a measuring point is correct.

According to one illustrative aspect of the present disclosure, there may be provided an X-ray fluorescence analyzer comprising: a sample stage on which a sample is placed; a sample moving mechanism configured to move the sample stage; an X-ray source configured to irradiate the sample with a primary X-ray; a detector configured to detect a fluorescent X-ray generated from the sample irradiated with the primary X-ray; an imaging device configured to image the sample on the sample stage; a display device which displays the image obtained by the imaging device on a screen; a pointing device configured to designate a specific position on the screen for allowing an input at the specific position; an image processing device configured to display a mark at the input position on the screen by the pointing device; and a control device configured to: control the sample moving mechanism and the image processing device; and when the sample stage is moved by the sample moving mechanism, control the image processing device to display the mark on the screen with moving the mark in the same moving direction as that of the sample stage by the same moving distance.

In the X-ray fluorescence analyzer, when a sample stage is moved by a sample moving mechanism, since a control device causes an image processing device to move a mark on a screen by the same moving distance and in the same moving direction as that of the sample stage so as to be displayed, the mark on the screen is moved in the same way in accordance with the movement of the sample stage, and thus a relative position between the sample and the mark on the screen is displayed without being shifted. Accordingly, the operator can simply perform the positioning of an X-ray radiation point with respect to the sample by setting the mark such as numbers, pictures (drawings), characters, and symbols as a reference point, even when the sample stage is moved.

The control device may be configured to control the image processing device to display a number as the mark in a case where a plurality of the samples are placed in a line on the sample stage.

That is, in such an X-ray fluorescence analyzer, when the plurality of samples are placed in a line on the sample stage, the control device can display a number as the mark, and thus, if the order of the samples corresponding to the position designated by the pointing device, that is, the order of numbers when counting from the end of the samples in a line is displayed on the screen, it is possible to easily confirm what number of the samples is being checked.

The imaging device may have a function of changing display magnification of an image to a certain display magnification by changing imaging magnification of the sample. The image processing device may be configured to display the mark at the input position corresponding to the imaging magnification.

That is, in the X-ray fluorescence analyzer, since the image processing device displays the mark at the input position corresponding to the imaging magnification, even in a case where the imaging magnification is changed, it is possible to set the mark, which is displayed on the screen in accordance with the imaging magnification, as a reference point.

The control device may have a function of storing a screen on which the mark is displayed as image data.

That is, in the X-ray fluorescence analyzer, since the control device has a function of storing the screen on which the mark is displayed as image data, even after the measurement is performed by the image data of the screen on which the sample and the mark are displayed at the same time, it is possible to easily confirm which sample has been measured.

The control device may have a function of storing position data of the mark corresponding onto the sample stage based on the input position and the image on the screen. After the mark is moved out of a display area of the screen due to the movement of the sample stage, when the mark based on the position data of the mark is positioned within the display area again due to a further movement of the sample stage, the image processing device may display the mark in the display area again based on the position data of the mark.

That is, in the X-ray fluorescence analyzer, after the mark is moved out of a display area of the screen and thus is not displayed on the screen due to the movement of the sample stage, the image processing device displays the mark in the display area again based on the position data of the mark when the position of the mark based on the position data of the mark is positioned within the display area again due to the movement of the sample stage, and thus even in the case where as the mark is moved out of the display area on the screen, the sample stage is moved, or a display image is scaled, it is possible to display the mark in the display area when returning to an original position or the display magnification.

The control device may have: a function of storing the position data of the sample on the sample stage based on the image and the position data of the mark corresponding onto the sample stage based on the input position on the screen; and a function of displaying the mark at the same position on the screen based on the position data of the mark when new samples are placed at the same position as that of the previously measured sample on the sample stage based on the position data of the sample.

That is, when placing new samples at the same position as that of the previously measured samples on the sample stage, the X-ray fluorescence analyzer has a function of displaying the mark overlapping the obtained image on the display device based on the stored position data, and thus even when new samples are placed at the same position as that of the previously measured samples on the sample stage, it is possible to specify a measuring point without displaying the mark by inputting a position again by the pointing device, thereby further improving the operability.

According to another illustrative aspect of the present disclosure, there may be provided a method of displaying a sample of an X-ray fluorescence analyzer comprising imaging a sample which is placed on a sample stage by an imaging device, displaying the obtained image on a display device, performing positioning of X-ray irradiation with respect to the sample by moving the sample stage, and then performing measurement or analysis, the method comprising: obtaining an image of the sample by the imaging device; displaying the image on the screen of the display device by an image processing device; receiving an input of a mark to a certain position on the screen by a pointing device; and displaying the mark on the screen synchronized with the movement of the sample stage, in which the mark is moved by the same moving distance and in the same moving direction as that of the sample stage by the image processing device.

The method may further comprise displaying the mark on the input position corresponding to image magnification by the image processing device when the imaging device changes display magnification of an image to a certain display magnification by changing the imaging magnification of the sample.

The method may further comprise: storing position data of the mark corresponding onto the sample stage based on the input position and the image on the screen; and after the mark is moved out of a display area of the screen due to the movement of the sample stage, when the mark based on the position data of the mark is positioned within the display area again due to a further movement of the sample stage, controlling the image processing device to display the mark in the display area again based on the position data of the mark.

The method may further comprise: storing the position data of the sample on the sample stage based on the image and the position data of the mark corresponding onto the sample stage based on the input position on the screen; and re-displaying the mark at the same position on the screen based on the position data of the mark when new samples are placed at the same position as that of the previously measured sample on the sample stage based on the position data of the sample.

According to the disclosure, the following effects can be achieved.

That is, according to an X-ray fluorescence analyzer and a method of displaying a sample thereof of the present disclosure, when a sample stage is moved by a sample moving mechanism, since a mark is moved by the same moving distance and in the same moving direction as that of the sample stage so as to be displayed on a screen by an image processing device, it is possible to simply match the position of an X-ray radiation point with the sample by setting the mark on the screen as a reference point. Particularly, even when each of a plurality of samples having the same shape as each other are in a line, a desired sample to be measured can be found by setting the mark on the screen as the sign. Therefore, it is possible to simply confirm whether or not the measuring point is correct from the screen.

BRIEF DESCRIPTION OF THE DRAWINGS

In the accompanying drawings:

FIG. 1 is an entire configuration diagram schematically illustrating an embodiment of an X-ray fluorescence analyzer and a method of displaying a sample thereof according to the present disclosure;

DETAILED DESCRIPTION OF THE PREFERRED EMBODIMENTS

Hereinafter, an embodiment of an X-ray fluorescence analyzer and a method of displaying a sample thereof according to the present disclosure will be described with reference to FIG. 1 and FIGS. 2A and 2B and FIGS. 3A and 3B.

Figure 2A:
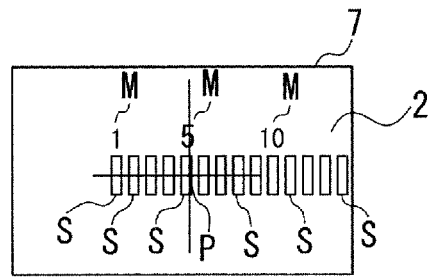
FIGS. 2A and 2B is a display example illustrating before and after the movement of a sample and a mark on a screen by a display unit in the present embodiment.
Figure 2B:
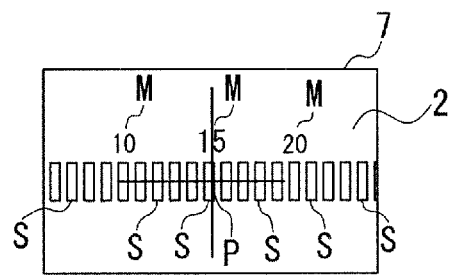
Figure 3A:
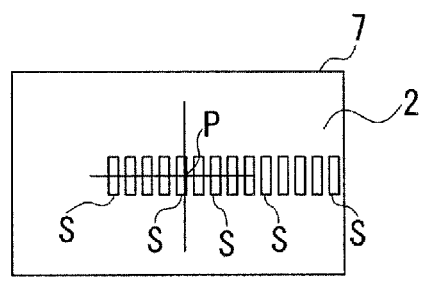
FIGS. 3A and 3B is a display example of the sample on the screen by the display unit in the related example of the X-ray fluorescence analyzer and the method of displaying the sample thereof according to the disclosure.
Figure 3B:
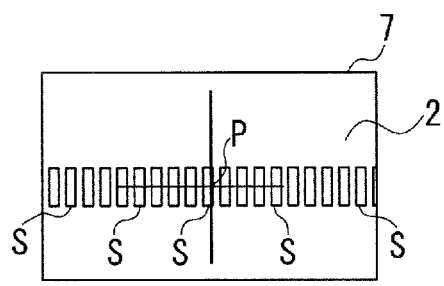

An X-ray fluorescence analyzer 1 of the embodiment is provided with, as illustrated in FIG. 1 and FIGS. 2A and B, a sample stage 2 which is capable of placing a sample S, a sample moving mechanism 3 which is capable of moving the sample stage 2, an X-ray source 4 which irradiates the sample S with a primary X-ray X1, a detector 5 which detects a fluorescent X-ray X2 generated from the sample S being irradiated with the primary X-ray X1, an imaging unit 6 which images the sample S on the sample stage 2, a display unit 7 which displays an image obtained by the imaging unit 6 on a screen, a pointing device 8 which is capable of designating and inputting a specific position on the screen, an image processing unit 9 which displays a mark M at the position on the screen which is input by the pointing device 8, and a control unit C which controls the sample moving mechanism 3 and the image processing unit 9.

When the sample stage 2 is moved by the sample moving mechanism 3, the above described control unit C has a function of controlling the image processing unit 9 to move the mark M on the screen by the same moving distance and in the same moving direction as that of the sample stage 2 and to display the mark M on the screen. That is, the control unit C causes the mark M which is displayed synchronously with the movement of the sample stage 2 on the screen of the display unit 7 to be relatively moved with the sample S.

Particularly, as illustrated in FIGS. 2A and B, when a plurality of samples S are placed in a line on the sample stage 2, the control unit C is capable of displaying the number as the mark M.

In addition, the above-described imaging unit 6 has a function of changing display magnification of an image to a certain display magnification by changing the imaging magnification of the sample S.

Further, the image processing unit 9 has a function of displaying the mark M at the input position corresponding to the imaging magnification. For example, even in a case where the imaging magnification becomes greater and thus the display magnification of the image which is displayed on the screen of the display unit 7 becomes greater, the mark M is displayed at the same position of the sample stage 2 on the screen synchronously with the magnification.

In addition, the control unit C has a function of storing the screen on which the mark M is displayed as image data.

In addition, the control unit C has a function of storing position data of the mark M corresponding onto the sample stage 2 based on the input position and the image on the screen. That is, the control unit C analyzes to which position on the sample stage 2 the input position of the mark M on the screen corresponds from the image data, and then stores the positional information of the mark M on the sample stage 2 as data.

Further, after the mark M is moved out of a display area of the screen and thus is not displayed on the screen due to the movement of the sample stage 2, the image processing unit 9 has a function of displaying the mark M in the display area again based on the position data of the mark M when the position of the mark M based on the position data of the mark M is positioned within the display area again due to the movement of the sample stage 2.

Further, the control unit C has a function of storing the position data of the sample S on the sample stage 2 based on the image and the position data of the mark M corresponding to the sample stage 2 based on the input position on the screen, and a function of displaying the mark M at the same position on the screen based on the position data of the mark M when placing new samples S at the same position as that of the previously measured sample S on the sample stage 2 based on the position data of the sample S.

In addition, the X-ray fluorescence analyzer 1 is provided with an analyzer 10 which is connected to the detector 5 and analyzes a signal from the detector 5, and a housing 11 which accommodates the X-ray source 4, the detector 5, the imaging unit 6, the sample stage 2, and the sample moving mechanism 3 therein.

The plurality of samples S can be placed on the sample stage 2, and are placed on the sample moving mechanism 3 which is an XY stage capable of advancing and retreating in at least a surface direction (X direction and Y direction).

The above-described imaging unit 6 which is an observation camera equipped with a CCD or the like is placed on an upper portion of the sample stage 2, and can image the samples S arranged on the sample stage 2.

The above-described X-ray source 4 is an X-ray tube which can irradiate the sample S with the primary X-ray X1, in which a thermionic emission, which is generated from a filament (a cathode) in the tube, is accelerated by a voltage applied between the filament (the cathode) and a target (an anode) and is then collided with W (tungsten), Mo (molybdenum) and Cr (chromium) of the target, resulting in generating the X-ray, and the generated X-ray is emitted from a window such as beryllium foil as the primary X-ray X1.

The above-described detector 5 is provided with a semiconductor detecting element (for example, a Si (silicon) element which is a pin structure diode (not shown)) which is placed in an X-ray incident window (not shown), and, when one X-ray photon is incident, generates a current pulse corresponding to this X-ray photon. The instantaneous current value of this current pulse is proportional to the energy of the incident characteristic X-ray. In addition, the detector 5 is set to output a signal by converting the current pulse generated from the semiconductor detecting element into a voltage pulse and amplifying the voltage pulse.

The above described analyzer 10 is a pulse height analyzer (a multichannel analyzer) which generates energy spectra, by obtaining the wave height of the voltage pulse from the signal.

The above-described control unit C is a computer which is formed of a CPU, and is connected to each unit such as the X-ray source 4, the detector 5, and the display unit 7 so as to control these units. In addition, the control unit C has a function of displaying the analysis result on the display unit 7.

Examples of the pointing device 8 can employ a mouse, a track ball, a touch pad, and the like. The pointing device 8 may be provided on the display unit 7 (e.g., touchscreen). In the embodiment, a mouse is used as the pointing device 8.

The above-described mark M is a sign such as numbers, pictures (drawings), characters, or symbols, and may be input by using a keyboard after designating the position by the pointing device 8 or may be set to be directly input by drawing a line on the screen by the pointing device 8.

In the above-described display unit 7, cross lines are indicated at the center, and an intersection point of this cross lines are set to be an X-ray radiation point P.

Next, a method of displaying the sample by using the X-ray analyzer 1 of the embodiment will be described.

The method of displaying the sample in the embodiment is a method of imaging the sample S which is placed on the sample stage 2 by the imaging unit 6, displaying the obtained image on the display unit 7, performing the positioning of the X-ray irradiation with respect to the sample S by moving the sample stage 2, and then performing the measurement or analysis. The method of displaying the sample includes an imaging step of obtaining an image of the sample S by the imaging unit 6, a display step of displaying the image on the screen of the display unit 7 by the image processing unit 9, an input step of inputting the mark M to a certain position on the screen by the pointing device 8, and a display synchronizing step of displaying the mark M on the screen which is moved by the same moving distance in the same moving direction as that of the sample stage 2 by the image processing unit 9 when moving the sample stage 2.

Hereinafter, a procedure of measuring the plurality of samples S in the X-ray analyzer 1 by using the method of displaying the sample of the embodiment will be described in detail.

For example, as illustrated in FIG. 2A, when the plurality of samples S are arranged in a line on the sample stage 2, the numbers are input on the screen of the display unit 7 as the mark M by the pointing device 8. That is, among the samples S in a line, "1" is input as the mark M which is the first sample S to the vicinity of the upper portion of a left-most end of the sample S which is designated by the pointing device 8, and then displayed on the screen.

With this, the sample S and the mark M are displayed as superimposed on the screen. Next, "5" is input as the mark M which is the fifth sample S to the vicinity of the upper portion of the fifth sample S from the left end, and then displayed on the screen. In addition, the vicinity of the upper portion of the sample S is designated by the pointing device 8 at an interval of every five samples S, the number of the sample S when counting the number from the left end is input to the designated vicinity of the upper portion of the sample S as the mark M, and then displayed on the screen.

In this way, as the mark M, the number is input in the vicinity of the sample S every five samples and then displayed on the screen of the display unit 7. In this state, among these samples S, when performing the sampling measurement at a certain interval of samples, for example, every ten samples, first, the fluorescent X-ray analysis of the sample S is performed by positioning an X-ray radiation point P with respect to the sample S, on which the mark M of "5" is displayed, by the sample moving mechanism 3. At this time, the control unit C controls the image processing unit 9 to move the mark M on the screen synchronously with the movement of the sample stage 2 by the same distance in the same direction. With this, the mark M on the screen is relatively moved with the sample S in accordance with the positioning performed by the sample moving mechanism 3.

Next, the fluorescent X-ray analysis of the sample S is performed by moving the sample stage 2 to the left by the sample moving mechanism 3, and positioning the X-ray radiation point P with respect to the sample S on which the mark M of "15" is displayed. Even at this time, the control unit C controls the image processing unit 9 to move the mark M with the sample S in accordance with the movement of the sample stage 2 and to display the mark M on the screen. Meanwhile, even in a case where the mark M is moved out of the screen due to the movement of the sample stage 2, the mark M is displayed again at the corresponding position on the screen if the sample stage 2 is moved to the original position again. With this, by setting the number of the mark M every ten samples as a reference point, the sample stage 2 is moved by the sample moving mechanism 3, and thus it is possible to easily perform the positioning of the X-ray radiation point P with respect to the sample S to be measured.

In addition, even in a case where a wide area image is displayed so as to input the mark M to a target position of the sample S to be measured, and then the image magnification is changed to a certain magnification of the image to be measured, the mark M is displayed at the input target position. In a wide area image, when the mark M is input to the target position of the sample S to be measured, it is possible to clearly recognize which part in the entirety is set to the position to be measured. Accordingly, even when the magnification of the sample image is increased while such an advantage remains, if the input mark M is displayed at the target position, it is possible to accurately confirm the position to be measured since the mark M is synchronized with the sample S even in a case where the sample S which is temporarily moved out of an area of the visual field displayed by zooming in or zooming out the display image is returned into the area of the visual field again. The size of the mark M being displayed at that time can be set to an easily visible size by fixing the size to the original magnification or measurement magnification, or changing the size in accordance with the magnification. Meanwhile, the input mark M is displayed at the target position in accordance with the movement of the sample stage 2, even in a case where the sample S which is temporarily moved out of the area of the visual field is returned into the area of the visual field again.

Meanwhile, the control unit C stores the screen on which the mark M is displayed on the display unit 7 with the sample S at the same time of performing each measurement, as image data. Accordingly, after performing the measurement by using the image data of the screen on which the sample S and the mark M are displayed together, it is possible to easily confirm which of samples S has been measured.

In addition, when a new sample S having the same shape is measured after the measurement of the sample S is completed, the new sample S is placed at the same position of the previously measured sample stage 2, the mark M which is stored in the control unit C is displayed on the screen of the display unit 7 based on the stored position data. Accordingly, it is possible to measure the new sample S in the same manner by setting the mark M, which is displayed at the same position where the previously measured sample S was measured, as a reference point.

As described above, in the X-ray fluorescence analyzer 1 and the method of displaying the sample thereof of the embodiment, when moving the sample stage 2 by the sample moving mechanism 3, the mark M on the screen is moved by the same moving distance and in the same moving direction as that of the sample stage 2 and displayed by the image processing unit 9, and thus, similarly, by moving the mark M on the screen in accordance with the movement of the sample stage 2, a relative position between the sample S and the mark M on the screen is displayed without being shifted. Accordingly, the operator can simply perform the positioning of the X-ray radiation point P with respect to the sample S by setting the mark M such as numbers, pictures (drawings), characters, and symbols as a reference point, even when the sample stage 2 is moved.

In addition, when the plurality of samples S are placed in a line on the sample stage 2, the control unit C can display the number as the mark, and thus, if the order of the samples S corresponding to the position designated by the pointing device 8, that is, the order of number when counting from the end of the samples in a line is displayed on the screen, it is possible to easily confirm the number of the samples S. Particularly, the plurality of samples S which have the same shape as each other are arranged in a line on the sample stage 2, and thus these samples S are suitable for performing the sampling analysis at an interval of every other number.

In addition, the image processing unit 9 displays the mark M at the input position corresponding to the imaging magnification, and thus even when the imaging magnification is changed, it is possible to set the mark M as a reference point in accordance with the changed imaging magnification.

Further, after the mark M is moved out of the display area of the screen and thus is not displayed on the screen due to the movement of the sample stage 2, the image processing unit 9 displays the mark M in the display area again based on the position data of the mark M when the position of the mark M based on the position data of the mark M is positioned within the display area again due to the movement of the sample stage 2, and thus even in the case where as the mark M is moved out of the display area on the screen, the sample stage 2 is moved, or a display image is scaled, it is possible to display the mark M in the display area when returning to an original position or the display magnification.

In addition, the control unit C has a function of storing the screen on which the mark M is displayed as the image data, and thus it is possible to easily confirm which of sample S has been measured even after the screen on which the sample S and the mark M are displayed together is measured by using the image data.

Further, when placing new samples S at the same position as that of the previously measured samples S on the sample stage 2, the X-ray fluorescence analyzer has a function of displaying the mark M overlapped with the obtained image on the display unit 7 based on the stored position data, and thus it is possible to display the previous mark M at the same position as before when the new samples S are placed to be measured. Accordingly, it is no longer necessary to newly input the position by the pointing device 8 whenever the new samples S are placed so as to display the mark, thereby further improving the operability.

Note that, the technical scope of the present disclosure is not limited to the above-described embodiment, and various modifications are possible within the scope of the disclosure.

For example, in the above described embodiment, the pulse height analyzer is applied to an energy dispersion type of X-ray fluorescence analyzer which measures the energy and strength of the X-ray, but may be applied to a wavelength dispersion type of X-ray fluorescence analyzer which measures the wavelength and strength of the X-ray by dispersing the fluorescent X-ray by using a spectral crystal.

In addition, in the above-described embodiment, the X-ray source and the detector are disposed on the upper side of the sample, but may be disposed on the lower side of the sample stage so as to perform the analysis or measurement of the lower side of the sample. Further, the detector may be a vacuum-tube type.

In addition, in the above described embodiment, the disclosure is applied to measure the plurality of samples which are arranged in a line on the sample stage, but may also measure a plurality of points of line patterns which are formed on the sample such as a semiconductor device or an electronic component on the sample stage. In this case, it is possible to easily confirm the measuring points in the line patterns by inputting the mark in the plurality of points of line patterns which are displayed on the screen of the display unit or in the vicinity of the line patterns, by the pointing device to display the input mark on the screen.

What is claimed is:

1. An X-ray fluorescence analyzer comprising:
   a sample stage on which a sample is placed;
   a sample moving mechanism configured to move the sample stage;
   an X-ray source configured to irradiate the sample with a primary X-ray;
   a detector configured to detect a fluorescent X-ray generated from the sample irradiated with the primary X-ray;
   an imaging device configured to image the sample on the sample stage;
   a display device which displays the image obtained by the imaging device on a screen;
   a pointing device configured to designate a specific position on the screen for allowing an input at the specific position;
   an image processing device configured to display a mark at the input position on the screen by the pointing device; and
   a control device configured to:
   control the sample moving mechanism and the image processing device; and
   when the sample stage is moved by the sample moving mechanism, control the image processing device to display the mark on the screen with moving the mark in the same moving direction as that of the sample stage by the same moving distance;
   wherein the control device has a function of storing position data of the mark corresponding onto the sample stage based on the input position and the image on the screen, and
   wherein after the mark is moved out of a display area of the screen due to the movement of the sample stage, when the mark based on the position data of the mark is positioned within the display area again due to a further movement of the sample stage, the image processing device displays the mark in the display area again based on the position data of the mark.

2. The X-ray fluorescence analyzer according to claim 1, wherein the control device is configured to control the image processing device to display a number as the mark in a case where a plurality of the samples are placed in a line on the sample stage.

3. The X-ray fluorescence analyzer according to claim 1, wherein the imaging device has a function of changing display magnification of an image to a certain display magnification by changing imaging magnification of the sample, and
   wherein the image processing device is configured to display the mark at the input position corresponding to the imaging magnification.

4. The X-ray fluorescence analyzer according to claim 1, wherein the control device has a function of storing a screen on which the mark is displayed as image data.

5. The X-ray fluorescence analyzer according to claim 1, wherein the control device has:
   a function of storing the position data of the sample on the sample stage based on the image and the position data of the mark corresponding onto the sample stage based on the input position on the screen; and a function of displaying the mark at the same position on the screen based on the position data of the mark when new samples are placed at the same position as that of the previously measured sample on the sample stage based on the position data of the sample.

6. A method of displaying a sample of an X-ray fluorescence analyzer comprising imaging a sample which is placed on a sample stage by an imaging device, displaying the obtained image on a display device, performing positioning of X-ray irradiation with respect to the sample by moving the sample stage, and then performing measurement or analysis, the method comprising:
    obtaining an image of the sample by the imaging device;
    displaying the image on the screen of the display device by an image processing device;
    receiving an input of a mark to a certain position on the screen by a pointing device; and
    displaying the mark on the screen synchronized with the movement of the sample stage, in which the mark is moved by the same moving distance and in the same moving direction as that of the sample stage by the image processing device;
    storing position data of the mark corresponding onto the sample stage based on the input position and the image on the screen; and
    after the mark is moved out of a display area of the screen due to the movement of the sample stage, when the mark based on the position data of the mark is positioned within the display area again due to a further movement of the sample stage, controlling the image processing device to display the mark in the display area again based on the position data of the mark.

7. The method of displaying a sample of an X-ray fluorescence analyzer according to claim 6, further comprising:
    displaying the mark on the input position corresponding to image magnification by the image processing device when the imaging device changes display magnification of an image to a certain display magnification by changing the imaging magnification of the sample.

8. The method of displaying a sample of an X-ray fluorescence analyzer according to claim 6, further comprising:
    storing the position data of the sample on the sample stage based on the image and the position data of the mark corresponding onto the sample stage based on the input position on the screen; and
    re-displaying the mark at the same position on the screen based on the position data of the mark when new samples are placed at the same position as that of the previously measured sample on the sample stage based on the position data of the sample.

* * * * *